Figure 1:
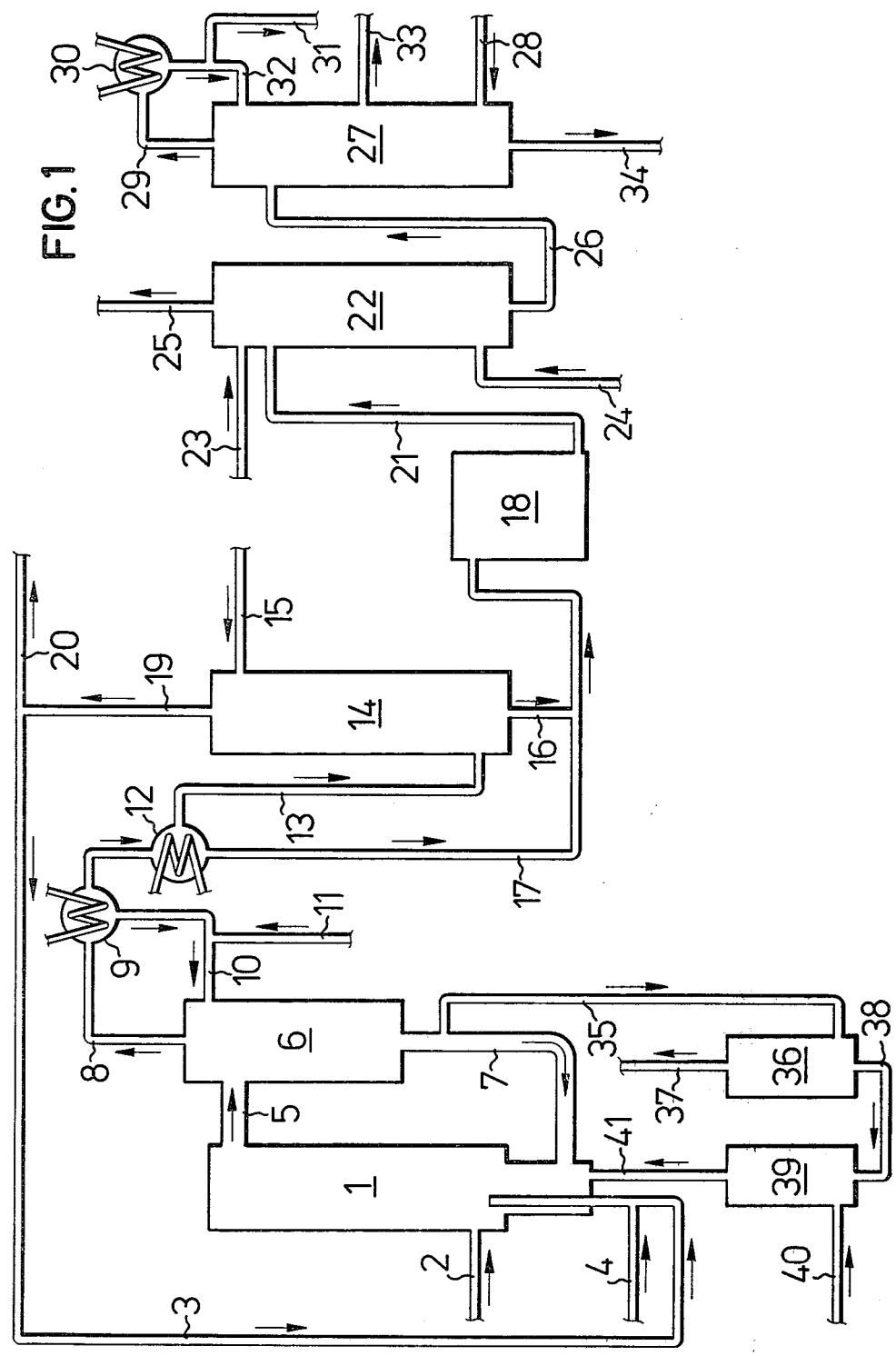

United States Patent [19]

Steppich et al.

[11] 4,237,073
[45] Dec. 2, 1980

[54] PROCESS FOR THE MANUFACTURE OF ACETALDEHYDE

[75] Inventors: Walter Steppich, Wiesbaden; Rudolf Sartorius, Frankfurt am Main, both of Fed. Rep. of Germany

[73] Assignee: Hoechst Aktiengesellschaft, Frankfurt am Main, Fed. Rep. of Germany

[21] Appl. No.: 50,313

[22] Filed: Jun. 20, 1979

[30] Foreign Application Priority Data

Jun. 22, 1978 [DE] Fed. Rep. of Germany ....... 2827380

[51] Int. Cl.$^3$ ............................................. C07C 47/07
[52] U.S. Cl. ............................................. 568/401
[58] Field of Search .................................. 260/604 AC

[56] References Cited

U.S. PATENT DOCUMENTS

| | | |
|---|---|---|
| 3,076,032 | 1/1963 | Riemenschneider et al. ....... 260/604 AC |
| 3,119,875 | 1/1964 | Steinmetz et al. ............ 260/604 AC |
| 3,381,037 | 4/1968 | Ohmae et al. ................ 260/604 AC |

FOREIGN PATENT DOCUMENTS 938836 10/1963 United Kingdom ............. 260/604 AC

OTHER PUBLICATIONS

Farbwerke Hoechst "Derwent Belgian Patent Reports" vol. 65, Jun. 25, 1960 p. C3.
Jira, Blau, Grimm; Hydrocarbon Processing, Mar. 1976 pp. 97-100.

Primary Examiner—Werren B. Lone
Attorney, Agent, or Firm—Curtis, Morris & Safford

[57] ABSTRACT

Process for the manufacture of acetaldehyde by reaction of ethylene and oxygen in the presence of an aqueous solution of palladium and copper chloride, in which continuously part of the latter solution is regenerated by heating it outside of the reactor. The gaseous mixture leaving the reactor is treated (a) by cooling with recycling of the condensate formed to the reactor and completion of the water portion that has not condensed during cooling, by the addition of water to the reactor, (b) by washing of the cooled gas mixture with water whereby an aqueous acetaldehyde solution is obtained, (c) by extractive distillation of this solution using water as extraction agent. Next, pure acetaldehyde is obtained as an overhead product in a further distillation step. The water demand of step (b) and optionally additionally of steps (a) and/or (c) is satisfied with the waste water obtained in the bottoms of the last distillation step and the residual waste water in each case is discharged.

5 Claims, 2 Drawing Figures

PROCESS FOR THE MANUFACTURE OF ACETALDEHYDE

The single-stage manufacture of acetaldehyde by direct oxidation of ethylene in the gaseous phase in the presence of palladium chloride and water is known (cf. Jira, Blau, Grimm; Hydrocarbon Processing, March 1976, pages 97 to 100). The process is generally carried out in the following manner on an industrial scale: Ethylene is oxidized in a bubble column reactor containing an aqueous solution of $CuCl_2$, $CuCl$ and $PdCl_2$, with oxygen, in a cyclic process at 100° to 150° C. under a pressure from 1 to 6 bars (absolute pressure), preferably at 125° to 135° C. and under a pressure from 3 to 4.5 bars (absolute pressure), to yield acetaldehyde. By the term "single-stage manufacture" there is to be understood that the oxidation of the ethylene yielding acetaldehyde and the reoxidation of the palladium chloride reduced in this process (said reoxidation being effected by $CuCl_2$ which is converted into CuCl, the latter in its turn is reoxidized by the oxygen) are carried out in one reactor. The gas current leaving the reactor and containing steam, acetaldehyde, ethylene and small amounts of oxygen, carbon dioxide, acetic acid, crotonaldehyde and chlorinated compounds (such as methyl chloride, ethyl chloride and chloroacetaldehydes) is cooled in a condenser to about 80° to 130° C., preferably to about 105° to 115° C. The condensate formed thereby substantially consisting of water, small amounts of acetaldehyde and acetic acid is generally recycled to the reactor.

Small amounts of copper oxalate and high molecular byproducts likewise formed remain persistent in the catalyst solution whereas the volatile by-products in conjunction with the acetaldehyde and the unreacted starting compounds leave the reactor. In order to avoid an accumulation of these by-products a small amount of the liquid phase is withdrawn continuously from the reactor. Next, this portion is released from pressure, whereby the dissolved low-boiling compounds such as acetaldehyde, ethylene and carbon dioxide flash and are removed. The degassed solution is conveyed to a regeneration vessel, where it is heated to a temperature from about 165° to 180° C., for example with the aid of introduced steam ("direct steam"), copper oxalate and the high-molecular by-products being decomposed thereby with the formation of water and carbon dioxide. The regenerated solution is recycled to the reactor.

The gas current leaving the reactor, after having been cooled in the condenser, is generally cooled further to about +30° to 80° C., preferably to 40° to 50° C., in heat exchangers. Next, the acetaldehyde is washed out from the gas current in a washing tower. The residual gas mainly consisting of ethylene, oxygen, carbon dioxide and inert gas is recycled to the reactor, after having removed part of this gas (in order to avoid an accumulation of carbon dioxide and inert gas) and after having added fresh ethylene. The condensate formed in the heat exchangers and the aqueous acetaldehyde solution formed in the washing tower are combined in a collecting vessel. This mixture designated as "crude aldehyde" is conveyed to a two-stage distillation process. In this process the low-boiling compounds (methyl chloride, ethyl chloride), and the dissolved gases such as ethylene and carbon dioxide are obtained as the overhead in a first step by extractive distillation using water as an extraction agent. The bottom product is passed to the second distillation step, where pure acetaldehyde is obtained as the overhead product. A fraction containing mainly crotonaldehyde is withdrawn as a sidestream. The high-boiling by-products (in particular acetic acid and chloroacetaldehydes) and the water are withdrawn from the bottom. The removed mixture is designated as "waste water" hereinafter.

The heat demand of both distillation steps is generally satisfied by introducing steam into the sumps ("direct steam heating"). For this purpose about 1.3 tons of direct steam per ton of acetaldehyde are required.

To make sure that the washing out of acetaldehyde as specified above is as complete as possible, large amounts of water must be used. Consequently, the acetaldehyde concentration in the aqueous solution obtained which forms the main part of the crude aldehyde, is relatively low. Correspondingly high amounts of waste water are obtained in the sump of the second distillation step with the waste water containing in addition to the washing water the condensed steam resulting from the direct steam heating of both distillation steps. Per ton of acetaldehyde there are obtained from about 8 to 10 m$^3$ of waste water, 1.3 m$^3$ thereof attributable to the direct steam. The waste water contains acetic acid, carbonyl compounds (mainly condensation products of acetaldehyde and chloroacetaldehydes) and chlorinated organic compounds (mainly chloroacetaldehydes) and must, therefore undergo treatment to avoid pollution of the environment. The waste water is bio-degradable but this process requires considerable expenditures owing to the great quantities of waste water and to the high COD value.

It has been unexpectedly found that the waste water may be recycled. This means that in particular the acetaldehyde may be washed out from the gas current with the waste water. Moreover, losses by evaporation of the aqueous catalyst solution, due to the fact that water is discharged continuously from the reactor along with the reaction products may be compensated for by adding waste water instead of with completely demineralized water as previously required. Finally waste water may be used without difficulty in the first distillation step for the extractive distillation.

part of the waste water is discharged continuously to insure that impurities in the recycled waste water only concentrate to such a degree that an equilibrium is achieved.

The process according to the invention for the manufacture of acetaldehyde by reaction of ethylene and oxygen in the presence of an aqueous solution of palladium and copper chloride, in which a portion of the latter solution is continuously regenerated by heating it outside of the reactor and in which the gaseous mixture leaving the reactor is worked up (a) by cooling with recycling of the condensate formed to the reactor and completion of the water portion that has not condensed during cooling, by the addition of water to the reactor, (b) by washing of the cooled gas mixture with water whereby an aqueous acetaldehyde solution is obtained, (c) by extractive distillation of this solution using water as an extraction agent and (d) in which pure acetaldehyde is obtained as the overhead product in a further distillation step, comprises satisfying the water demand of step (b) and optionally additionally of steps (a) and/or (c) with the waste water obtained in the sump of the last distillation step and discharging the residual waste water.

Washing of the gas mixture as specified in step b results in an aqueous acetaldehyde solution which is carried out with waste water. Preferably, in addition either (1) the water discharged from the reactor in a gaseous state and which has not condensed during cooling is replaced by introducing waste water into the reactor or (2) the water demand of the extractive distillation (step c) is satisfied by using waste water. Most preferably measures (1) and (2) are both employed.

Prior to being recycled, the waste water is cooled to room temperature. The quantity of discharged waste water equals the quantity of make-up water. This means that when in step (a) and/or (c) fresh water is used, a corresponding quantity of waste water must be discharged. When using direct steam for heating the distillation steps (c) and/or (d) a corresponding quantity of waste water must likewise be discharged. When heating both distillation steps (c) and (d) with direct steam and when recycling the waste water to step (b) as well as to steps (a) and (c), which procedure is preferred, only the amount of water introduced via the direct steam needs to be discharged. The discharged water is generally biologically treated.

Excepting the fact that the waste water is recycled, the procedure is as described initially, in particular as regards the temperature ranges.

It is surprising that the water can be recycled, since an incomplete washing out of the acetaldehyde and disturbances in the reactor (formation of insoluble residues and catalyst damaging) were to be expected due to the impurities content of the waste water.

Moreover it was to be expected that when recycling the waste water the usual 1.3 tons of direct steam per ton of acetaldehyde for both distillation steps would be required. This is not the case, surprisingly. On the contrary, the quantity of water required for washing out the acetaldehyde is smaller when operating with recycled waste water than when operating with fresh water. It was to be expected that due to the impurities in the recycled water, a greater amount would be required for washing. However, the consumption of water is about 20% less than when using fresh water. As a consequence, the demand of direct steam for the two-step distillation of the crude aldehyde (which is in this case diluted to a lower degree) decreases by about 20%. It was moreover to be expected that the chloroacetaldehydes contained in the recycled water would be cleaved under the reaction conditions and that, consequently, the concentration of chlorine ions would increase. This increased concentration of chloride ions as well as the acetic acid contained in the recycled water would create corrosion problems for the plant. However, tests have shown that the chloroacetaldehydes are cleaved to a negligible degree only. The chromium-nickel steel usually employed for plants of this type satisfies the requirements when appropriately processed and the waste water may be recycled without modifying the material of the columns, that is to say, in existing plants.

A further surprising observation could be made during the analysis of the by-products contained in the discharged portion of the waste water. It was to be expected that the quantity of impurities formed during the recycling of the waste water according to the invention would be equal to that formed with the use of fresh water according to the state of the art. However, analysis of the impurities contained in the discharged waste water position revealed smaller quantities thereof than in waste water obtained with the use of fresh water.

The discharged waste water portion can be readily worked up by distillation. It has been found, that the impurities (with the exception of acetic acid) contained in this waste water can be largely separated as the overhead product of a column having the adequate dimensions, in this case the sump of the column comprising water which contains substantially acetic acid, and, hence, the biological treatment can be reduced. Considering the small difference of about 2° C. in the boiling points of the bottom and of the overhead product this was a surprising observation. The head product is suitably passed to the catalyst regeneration step, where it is completely decomposed into water, carbon dioxide and hydrochloric acid. In order to avoid misunderstandings it should be noted that "waste water" according to its above definition is the bottom product of the second distillation column. The "discharged" portion of waste water is either that portion of the waste water that is subjected to a biological treatment or which is only a relatively small portion of the overhead product, in comparison with the bottom product, which is recycled. In the latter case not the whole "discharged waste water" is recycled but a fraction thereof.

Figure 2:
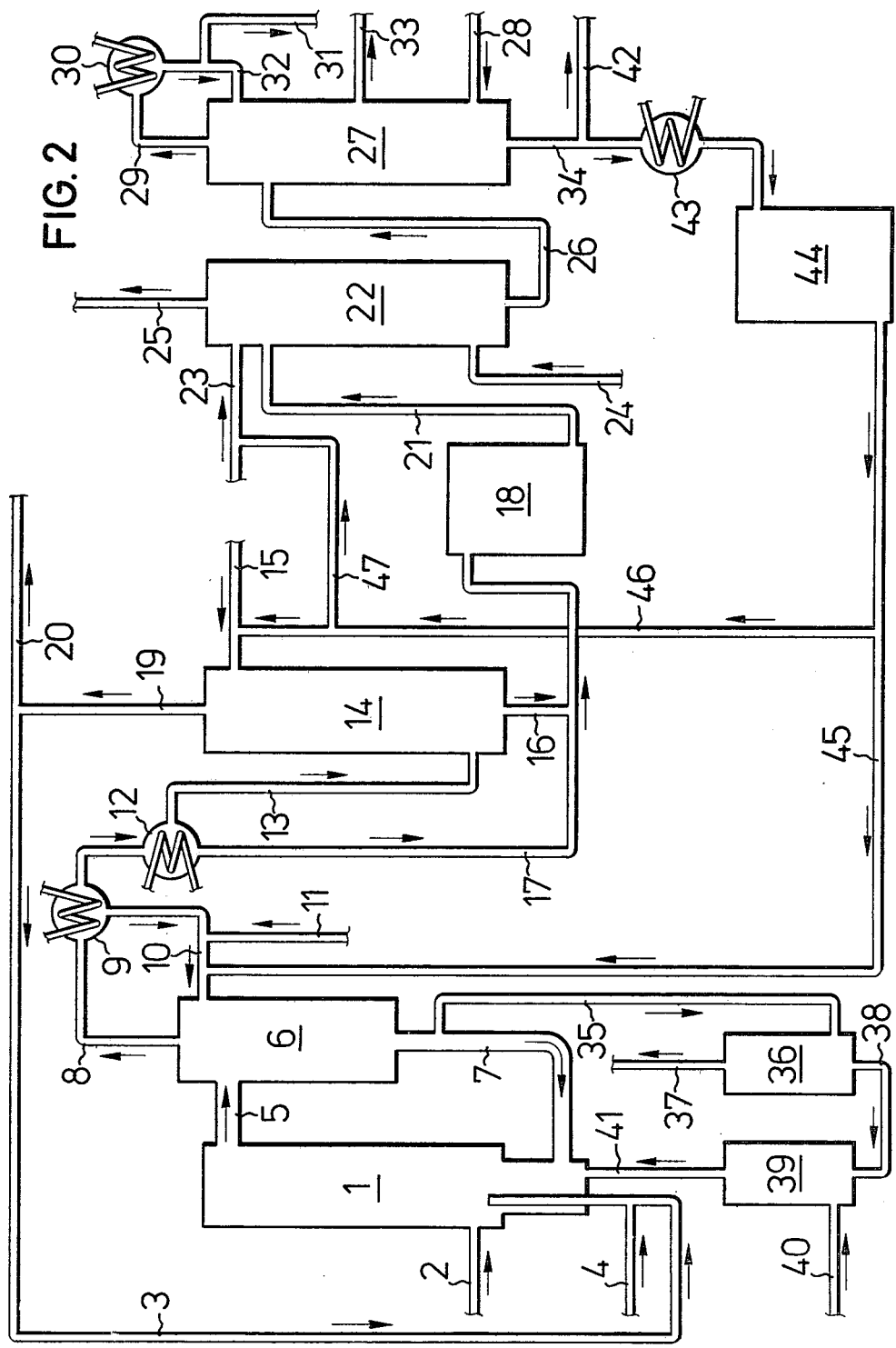

The present invention will be illustrated, by way of example, in FIG. 2 representing a flow scheme of the process of the invention and in the description referring thereto:

COMPARATIVE EXAMPLE:

(a) Apparatus arrangement (cf. FIG. 1)

An aqueous solution of $CuCl_2$, $CuCl$ and $PdCl_2$ is placed in reactor (1). Oxygen is added via conduit (2) and circulating gas, to which fresh ethylene has been added via conduit (4) is introduced via conduit (3). The gas-liquid mixture formed in the reactor and consisting of gaseous starting and final products and of the catalyst solution passes via tube (5) into separator (6), where the gaseous phase and the liquid phase are separated from each other. The liquid is recycled to reactor (1) via conduit (7). The gases leave the separator via conduit (8) and are cooled to 110° C. in precondenser (9). The condensate formed in this process is recycled to the reactor by passing successively via conduit (10) to the separator, after having added via conduit (11) demineralized water to compensate for the water of the catalyst solution discharged from the reactor in conjunction with the reaction products and via conduit (7). The gases that have not condensed in the precondenser (9) are further cooled in heat exchanger (12) and are then passed to washing tower (14) by passing over conduit (13). Acetaldehyde is washed out from the gases with water introduced via conduit (15). The acetaldehyde solution formed passes via conduit (16) to collecting vessel (18) and the condensate formed in heat exchanger (12) passes via conduit (17) to vessel (18). The washed gases leave the washing tower at the top and are recycled to reactor (1) via conduit (19), after a portion thereof has been discharged as waste gas via conduit (20).

The mixture designated as "crude aldehyde" is conveyed to the first distillation column (22) from vessel (18) by passing through conduit (21) and is submitted to an extractive distillation with water. The quantity of water required for this purpose is introduced via conduit (23). The column is heated by steam introduced via conduit (24). The head product mainly consisting of methyl chloride, ethyl chloride, carbon dioxide and ethylene is withdrawn via conduit (25). The bottom product is conveyed to the second distillation column (27) via conduit (26), this column being likewise heated by direct steam which is introduced via conduit (28). Pure acetaldehyde is withdrawn as head product via conduit (29). After having condensed in heat exchanger (30), the main quantity of acetaldehyde is withdrawn via conduit (31) and part thereof is refluxed to column (27) via conduit (32). A fraction substantially consisting of crotonaldehyde is withdrawn at a lateral outlet (33). The high-boiling by-products (in particular acetic acid and chloroacetaldehydes) and the water are withdrawn at the bottom as "waste water" via conduit (34). Part of the liquid recycling to reactor (1) from separator (6) via conduit (7) is withdrawn continuously via conduit (35) and it is released from pressure in the expansion vessel (36). Thereby the dissolved low-boiling substances pass over in the gaseous phase and are removed via conduit (37). The degassed solution is conveyed to regenerator (39) via conduit (38), where it is heated to 170° C. by means of steam introduced via conduit (40). Next, the solution is recycled to reactor (1) via conduit (41).

(b) Test description

In the plant specified above there are prepared per hour 13 tons of acetaldehyde from 5.3 tons of oxygen and 9 tons of ethylene in the presence of a catalyst solution containing 100 tons of water, 100 kmols of $CuCl$ and $CuCl_2$ and 60 kg $PdCl_2$. The following quantities of water and steam were consumed in this process:

15 m³/h of completely demineralized water for the reactor (to compensate for the losses by evaporation), introduced via conduit (11), 77.5 m³/h of river or spring water to wash out the acetaldehyde, introduced via conduit (15), 1.5 tons/h of direct steam for the catalyst regeneration, introduced via conduit (40), 1.5 m³/h of completely demineralized water for the extraction in the first distillation column, introduced via conduit (23), 3 tons/h of direct steam for the first distillation column, introduced via conduit (24) and 14 tons/h of direct steam for the second distillation column introduced via conduit (28).

From these feed quantities of water and steam there results a waste water quantity of 112.5 m³/h, obtained as bottom product of column (27).

This waste water contains:

| | |
|---|---|
| 0.28% of acids (calculated as acetic acid) | 315 kg/h, |
| 0.036% of aldehydes (calculated as acetaldehydes), | 45 kg/h, |
| 200 ppm of organically bound chlorine (calculated as chloroacetaldehyde) | 49.7 kg/h |
| 2,700 mg of $O_2$/l COD, that is $O_2$ demand | 304 kg/h. |

The waste water is worked up biologically.

EXAMPLE 1:

(a) Apparatus arrangement (cf. FIG. (2)

The apparatus arrangement is identical to that in the Comparative Example, except that the waste water withdrawn via conduit (34) at the bottom of the second distillation column (27), after removal of part thereof via conduit (42) is recycled to the process via condenser (43) and storage vessel (44) by the following paths:

1. Via conduit (45) and conduit (10) to separator (6) to compensate for the evaporated water of the catalyst solution, (these losses were off set in the Comparative Example by the addition of completely demineralized water via conduit (11)).
2. To washing tower (14) by passing through conduit (46), that branches from conduit (45) and opens into conduit (15) (through this latter conduit fresh water had been introduced in the Comparative Example. In this procedure this addition is required only at the beginning of the process).
3. To the first distillation column (22) by passing through conduit (47) that branches from conduit (46) and opens into conduit (23) (in the Comparative Example fresh water had been introduced via the latter conduit. In this procedure this addition is required at the beginning of the process only).

(b) Test description

Analogously to the Comparative Example there are prepared per hour 13.0 tons of acetaldehyde with the sole difference that the main quantity of the waste water is recycled.

After steady state conditions are achieved, 15.7 m³/h (=16.6%) of the waste water obtained are discharged through conduit (42). This quantity corresponds to that of the condensate formed from the direct steam.

The major part of the waste water, namely 79 m³/h, that is 83.3% of the waste water obtained, is cooled to 15° to 20° C. and recycled.

The following water balance is achieved:

15 m³/h of water recycled to the reactor (to compensate for the losses by evaporation), introduced through conduit (45), 62.5 m³/h of recycled water to wash out the acetaldehyde, introduced through conduit (46), 1.5 tons/h of direct steam for the catalyst regeneration, introduced through conduit (40), 1.5 m³/h of recycled water for the extraction in the first distillation column, introduced through conduit (47), 1.7 tons/h of direct steam for the first distillation column introduced through conduit (24) and 12.5 tons/h of direct steam for the second distillation column introduced from conduit (28).

From this balance there results a total quantity of waste water of 94.7 m³/h.

The waste water discharged through conduit (42) contains:

| | |
|---|---|
| 1.7% of acids (calculated as acetic acid) | 267 kg/h, |
| 0.24% of aldehyde (calculated as acetaldehyde) | 38 kg/h, |
| 700 ppm of organically bound chlorine (calculated as chloroacetaldehyde) | 24.3 kg/h, |
| 18,000 mg of $O_2$/l COD, that is $O_2$ demand | 283 kg/h. |

The discharged waste water is worked up biologically.

EXAMPLE 2

Distillation treatment of the discharged portion of waste water

The procedure is as in Example 1, except that the quantity of waste water discharged through conduit (42) is fed to a column having 45 bubble trays.

The inlet is positioned at the 30th tray, calculated from the bottom. 2.79% of the feed quantity are withdrawn as distillate at the top with a reflux ratio of 1:3, an overhead temperature of 98° C. and a bottom temperature of 100° C.

Consequently, there are obtained 27.9 g of overhead product and 927.1 g of sump product per liter of feed substance.

The sump product contains the following components in addition to water:
1.75% of acids (calculated as acetic acid),
0.08% of aldehydes (calculated as acetaldehyde),
135 ppm of organically bound chlorine (calculated as chloroacetaldehyde), which corresponds to 0.03% and
15,400 mg of $O_2/l$ of COD.

The overhead product contains in addition to water:
0.05% of acids (calculated as acetic acid),
6.34% of aldehydes (calculated as acetaldehyde),
1.7% of organically bound chlorine (calculated as chloroacetaldehyde) which corresponds to 3.76%.

When producing 12.0 tons/h of acetaldehyde the following quantities of bottom and overhead product are formed:

| | |
|---|---|
| sump product of the distillative working up of the discharged waste water portion: | 15.3 m³/h, |
| overhead product of the distillative working up of the discharged waste water portion: | 438 kg/h. |

The sump product contains in addition to water:
268 kg/h of acids (calculated as acetic acid),
12.2 kg/h of organically bound chlorine (calculated as chloroacetaldehyde) and
236 kg/h of $O_2$ demand (COD).

The sump product is worked up biologically.

The overhead product of the working up column contains:
traces of acids,
16.5 kg/h of organically bound chlorine (calculated as chloroacetaldehyde),
27.6 kg/h of aldehydes (calculated as acetaldehyde) and
394 kg/h of water.

The heat product is introduced continuously into regenerator (39), where it is completely degraded under the test conditions to $CO_2$, water and HCl.

The following water balance is achieved:
14.6 m³/h of water recycled to the reactor
0.4 m³/h of head product of the waste water distillation (conveyed to the reactor via the regenerator),
62.5 m³/h of recycled water to wash out the acetaldehyde,
1.5 tons/h of direct steam for the catalyst regeneration,
1.5 tons/h of recycled water for the extraction in the first distillation column,
1.7 tons/h of direct steam for the first distillation column and
12.5 tons/h of direct steam for the second distillation column.

Hence, a total quantity of waste water of 79 m³/h is recycled as in Example 1. As prepurified waste water there are obtained 15.3 m³/h.

A comparison of the acid value with the COD value shows that the COD value is lower than that deduced theoretically from the acid content (calculated 272 kg/h, found 235 kg/h).

This difference is due to the fact that the titrimetrical determination of the acetic acid includes further non-oxidizable acids or acids consuming less oxygen such as formic acid.

The working up column may naturally be heated with direct steam as well. In this case the quantity of waste water obtained is increased by the amount of condensing direct steam.

| | Nature of added water | Purpose of water addition | Unit | Com. Ex. | Example 1 | Example 2 |
|---|---|---|---|---|---|---|
| reactor (1) | (a) completely desalted water | compensation for losses by evaporation | m³/h | 15.0 | — | — |
| | (b) recycled water | | m³/h | — | 15.0 | 14.6 |
| | (c) head product of waste water distillation | | m³/h | — | — | 0.4 |
| washing tower (14) | (a) fresh water | washing out of acetaldehyde | m³/h | 77.5 | — | — |
| | (b) recycled water | | m³/h | — | 62.5 | 62.5 |
| 1. distillation column (22) | (a) completely desalted water | extraction | m³/h | 1.5 | — | — |
| | (b) recycled water | | m³/h | — | 1.5 | 1.5 |
| | (c) steam | column heating | to/h | 3.0 | 1.7 | 1.7 |
| 2. distillation column (27) | steam | column heating | to/h | 14.0 | 12.5 | 12.5 |
| regenerator (39) | steam | catalyst regeneration | to/h | 1.5 | 1.5 | 1.5 |
| water to be worked up biologically | quantity | | m³/h | 112.5 | 15.7 | 15.3 |
| | COD | | kg O₂/h | 304 | 283 | 236 |
| | acids (calculated as acetic acid) | | kg/h | 315 | 267 | 267 |
| | aldehydes (calculated as acetaldehyde) | | kg/h | 45 | 38 | 12.2 |
| | organically bound chlorine (calculated as chloroacetaldehyde) | | kg/h | 49.7 | 24.3 | 4.6 |

What is claimed is:

1. In a process for the manufacture of acetaldehyde which includes reacting ethylene and oxygen in a reactor in the presence of an aqueous solution of palladium and copper chloride at a temperature of 100° to 150° C. and a pressure of 1.0 to 6.0 atmospheres to form a gaseous mixture, continuously regenerating a portion of said solution by heating said solution outside of the reactor, cooling the gaseous mixture to form a condensed and noncondensed portion, recycling the condensed portion to the reactor, adding water to either the condensed portion or directly to the reactor in an amount approximately equal to the amount of water present in the noncondensed portion, washing the noncondensed portion with water to form an aqueous acetaldehyde solution, separating the aqueous acetaldehyde solution by an extractive distillation step using water as an extraction agent and further separating the bottoms product of said extractive distillation step by a second distillation step to obtain substantially pure acetaldehyde as an overhead product and waste water as a bottoms product, the improvement comprising recycling a portion of the waste water to satisfy the water demand required to wash the noncondensed portion of the gaseous mixture and discharging any residual waste water.

2. The process of claim 1 wherein substantially all of the water added to the condensed portion of the gaseous mixture is waste water.

3. The process of claim 1 wherein substantially all of the water added directly to the reactor is waste water.

4. The process of claims 1, 2 or 3 wherein substantially all of the water added as an extraction agent in the extractive distillation step is waste water.

5. The process of claim 1 which further comprises separating the residual waste water to obtain an overhead product containing volatile impurities which is recycled to the regeneration step and a bottoms product of water substantially containing acetic acid.

* * * * *